(12) United States Patent
Paulus et al.

(10) Patent No.: US 8,774,360 B2
(45) Date of Patent: Jul. 8, 2014

(54) METHOD OF PROCESSING RADIATION SPECTRA DIFFUSED THROUGH A MATERIAL IN ORDER TO OBTAIN A PRIMARY DIFFUSE RADIATION SPECTRUM THROUGH SAID MATERIAL, ASSOCIATED DEVICE AND COMPUTER PROGRAM

(75) Inventors: Caroline Paulus, Saint-Martin D'Heres (FR); Jean Rinkel, Grenoble (FR); Joachim Tabary, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 398 days.

(21) Appl. No.: 13/222,971

(22) Filed: Aug. 31, 2011

(65) Prior Publication Data
US 2012/0051517 A1    Mar. 1, 2012

(30) Foreign Application Priority Data
Aug. 31, 2010 (FR) ...................................... 10 56912

(51) Int. Cl.
*G01T 1/36*    (2006.01)
(52) U.S. Cl.
USPC ............................................................ 378/83
(58) Field of Classification Search
USPC ...................................... 378/70, 83; 250/395
See application file for complete search history.

(56) References Cited

U.S. PATENT DOCUMENTS 6,320,933 B1    11/2001    Grodzins et al.
2009/0092307 A1    4/2009    Sabol et al.

FOREIGN PATENT DOCUMENTS

EP           1 566 771 A1    8/2005
WO    WO 2007/007247 A1    1/2007

OTHER PUBLICATIONS

French Preliminary Search Report regarding corresponding French Patent Application No. 1056912 dated Apr. 15, 2011 (2 pgs).
Lee, D. & Seung, H.S., 2001. Algorithms for Non-negative Matrix Factorization. *Adv. Neural Info. Proc. Syst.*, (13), 556-562.

*Primary Examiner* — Irakli Kiknadze
(74) *Attorney, Agent, or Firm* — Brinks Gilson & Lione

(57) ABSTRACT

A method and device for obtaining a first radiation spectrum diffused through a material, in which the material is exposed to an incident irradiation beam emitted by a radiation source. A first radiation spectrum diffused through the material is measured by means of a main detector, arranged so that its observation field intersects the irradiation beam inside the material. At least one secondary radiation spectrum diffused through the material is measured by means of at least one secondary detector and a measurements matrix (X) is constructed starting from previously measured spectra. The measurements matrix is decomposed in two non-negative matrices, a weights matrix (A) and a spectra matrix (S), where the spectra matrix includes an estimated multiple diffuse radiation spectrum and an estimated primary diffuse radiation spectrum. The device includes a microprocessor and computer program. A computer program product for implementing the method is also provided.

15 Claims, 10 Drawing Sheets

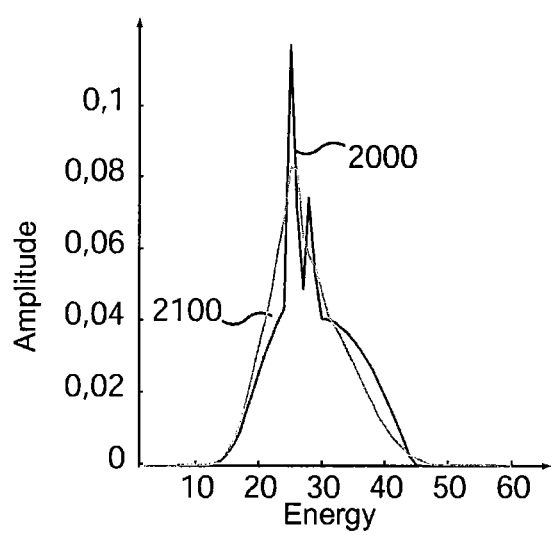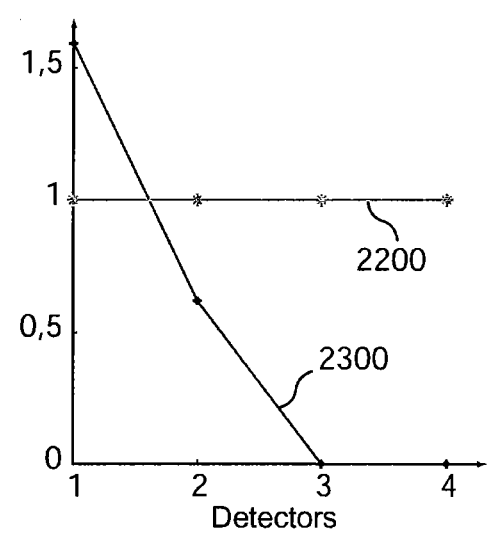
Fig. 10
Fig. 11

METHOD OF PROCESSING RADIATION SPECTRA DIFFUSED THROUGH A MATERIAL IN ORDER TO OBTAIN A PRIMARY DIFFUSE RADIATION SPECTRUM THROUGH SAID MATERIAL, ASSOCIATED DEVICE AND COMPUTER PROGRAM

PRIORITY CLAIM

This application claims priority to French Patent Application No. 1056912, filed Aug. 31, 2010, the contents of which are incorporated by reference herein.

TECHNICAL FIELD

The invention relates to a method for processing diffuse radiation spectra through a material and more in particular to a method for extracting a primary diffuse radiation spectrum from a set of at least two measured spectra of diffuse radiation through a material exposed to incident radiation. It relates also to an associated device and a computer program for this extraction process. The application domain of the invention extends in the first place to the spectrometry of diffuse X or gamma radiation, in particular employed in the analysis of materials. This type of spectrometry can be used for detecting explosives.

BACKGROUND

The diffusion spectrometry of X rays is based on exposing a material to incident X rays with energy equal to a few tens to a few hundreds keV. When they encounter the material on which they are projected, the X photons induce different types of interaction with the material: fluorescence or internal conversion (photoelectric effect during which the photon transfers all its energy to the material which returns it afterwards), inelastic diffusion, (or Compton effect which includes a change in the direction of the photon and a reduction of its energy), creation of positron-electron pairs (uniquely for X rays with very high energy not considered in the present invention), or Rayleigh diffusion (or elastic diffusion, a minority of the considered energies).

The invention uses electromagnetic radiation sources with energy between 0 and a few hundreds keV, for instance 300 keV. It can involve X ray generating tubes. Beyond 30 keV the Compton diffusion phenomenon is predominant for organic materials.

Certain characteristics of the studied materials (linear attenuation coefficient µ (E), density, ratio $$\frac{Z}{A}$$

between the atomic number Z and the atomic mass number A) can in principle be determined on the basis of theoretical knowledge and by obtaining the primary diffuse spectrum of the material exposed to X rays, in other words, the diffuse radiation spectrum which is obtained in a situation whereby each photon interacts only once with the material. The X diffusion spectra comprise an important component of diffuse photons that have interacted several times with the material. This component is called the multiple diffuse radiation spectrum.

Certain information, in particular the density of the material, can be obtained based on the total diffuse radiation spectrum because the attenuating character of the material affects in the same manner the two components, primary and multiple, of the diffuse radiation spectrum. To obtain a better estimate of this density, and other physical and chemical information, it is known that the use of the total diffuse radiation spectrum leads to imperfect results.

PCT Publication No. WO2007/007247 discloses the use of transmission data to determine the multiple diffuse radiation component.

The invention is placed in another context, because it applies in the first place to an analysis system with a strongly collimated radiation source, and a detector placed in such manner that it collects diffuse radiation.

This detector can be placed in the same half-space as the source opposite the surface of the material studied, and also strongly collimated. This is called a retro-diffusion configuration. The detector can also be placed in such manner that the studied material is situated between the source and the detector. This is called a diffusion configuration. In the last case, the collimation of the source and/or the detector avoids that the radiation transmitted through the material is not detected (in particular, not having interacted with the material).

U.S. Pat. No. 6,320,933 discusses an analysis of the diffusion of retro-diffuse X rays. The ratio of retro-diffuse intensities measured by a detector detecting all radiations and a detector measuring only the multiple diffuse radiation component gives only an estimate of the density. On the contrary, thanks to a specific processing algorithm, the invention described below distinguishes between the multiple diffuse radiation and the primary diffuse radiation and provides more numerous physical and chemical information.

SUMMARY

In the context of this analytic arrangement, the goal of the one embodiment of the disclosure is to remedy the problem mentioned above, by proposing a method for correcting the total diffuse radiation spectrum in order to extract from it the primary diffuse radiation. For this purpose, a method is proposed for processing spectra of diffuse radiations through a material in order to obtain a primary diffuse radiation spectrum through said material, in which the material is exposed to an incident radiation beam, emitted by a source of radiation and at least the diffuse radiation spectrum through the material is measured. The method according to the invention is characterized in that:

a primary diffuse radiation spectrum through the material is measured by means of a detector, called main detector, arranged in such manner that its observation field intersects the radiation beam inside the material, at least one other diffuse radiation spectrum through the material is measured, called secondary spectrum, by means of at least one detector called secondary detector, a matrix (X) is constructed, called measurements matrix, starting from the previously measured spectra, said measurements matrix is decomposed in two non-negative matrices, namely a matrix (A) called weights matrix and a matrix (S) called spectra matrix, the latter comprises an estimated multiple diffuse radiation spectrum and an estimated primary diffuse radiation spectrum.

An embodiment of the disclosure relates also to a device for processing diffuse radiation spectra in order to obtain a primary diffuse radiation spectrum through a material, comprising means suitable for implementing the method of the invention. In particular, the invention extends to a device for processing diffuse radiation spectra in order to obtain a primary diffuse radiation spectrum through a material, comprising a radiation source suitable for emitting a radiation beam incident towards the material, and at least one detector suitable for measuring a diffuse radiation spectrum through the material. The device according to the invention is such that it comprises:

- a first detector, called main detector, suitable for measuring a primary diffuse radiation spectrum through the material, and arranged in such manner that its observation field intersects the irradiation beam inside the material,
- at least one detector called secondary detector, suitable for measuring at least one other spectrum, called secondary spectrum, of diffuse radiation through the material,
- means for constructing a matrix (X) called measurements matrix, starting from the measured spectra,
- software means for decomposing said measurements matrix in two non-negative matrices, namely a matrix (A) called weights matrix and a matrix (S) called spectra matrix, the latter comprises an estimated multiple diffuse radiation spectrum and an estimated primary diffuse radiation spectrum.

To be noted that the main and secondary detectors can consist of distinct devices. In a variant, at least two of the detectors consist of one and the same device, which is moved during the method according to the invention, between two measurements of the spectra.

Advantageously, prior to decomposing the measurements matrix, the weights matrix is initialized by extrapolation of pre-established data for a plurality of reference materials. By preference, the extrapolation is performed using in essence an estimate of the density as extrapolation variable.

In addition, the spectra matrix (S) is initialized with primary and multiple diffuse radiation spectra simulated for one or more reference materials exposed to said radiation beam of the source.

The step of decomposing the measurements matrix in non-negative matrices can include an iterative process, each iteration comprising an update of the coefficients of said non-negative matrices. Said iterative process is continued until a convergence criterion is satisfied.

According to another aspect of the method according to the invention, at least one of the secondary spectra is advantageously a solely multiple diffuse radiation spectrum. In other words, this secondary spectrum does not contain a primary diffuse radiation, or in negligible quantity. In other terms, advantageously and according to the invention, at least one secondary detector is arranged in such manner that its observation field is not intersecting the radiation beam inside the material.

The device can contain in addition at least two collimated detectors with identical solid observation angle. It can comprise at least two collimated detectors and an incident collimated source of radiation, by preference the solid angles of the irradiation beam and of the observation field of said detector are identical. In the particular case of a device in which the source and the main detector are collimated, the observation field of the detector is then advantageously of the same dimension as the irradiation beam of the source at the location of their intersection.

Another embodiment of the disclosure extends also to a computer program comprising a sequence of instructions suitable, when executed by a microprocessor, for implementing a method according to the invention.

Yet another embodiment of the disclosure extends in addition to a method and a device characterized in combination by all or part of the characteristics described above and here after.

The various embodiments of the disclosure will now be described relative to the attached figures, provided as non-limiting illustrations.

BRIEF DESCRIPTION OF THE DRAWING

FIG. 10 illustrates the spectra used during the initialization of data for implementing the method according to the invention in the framework of the volume analysis of the material of FIG. 8.

FIG. 11 illustrates data used for implementing the method according to the invention in the framework of the volume analysis of the material of FIG. 9.

DETAILED DESCRIPTION

Figure 1:
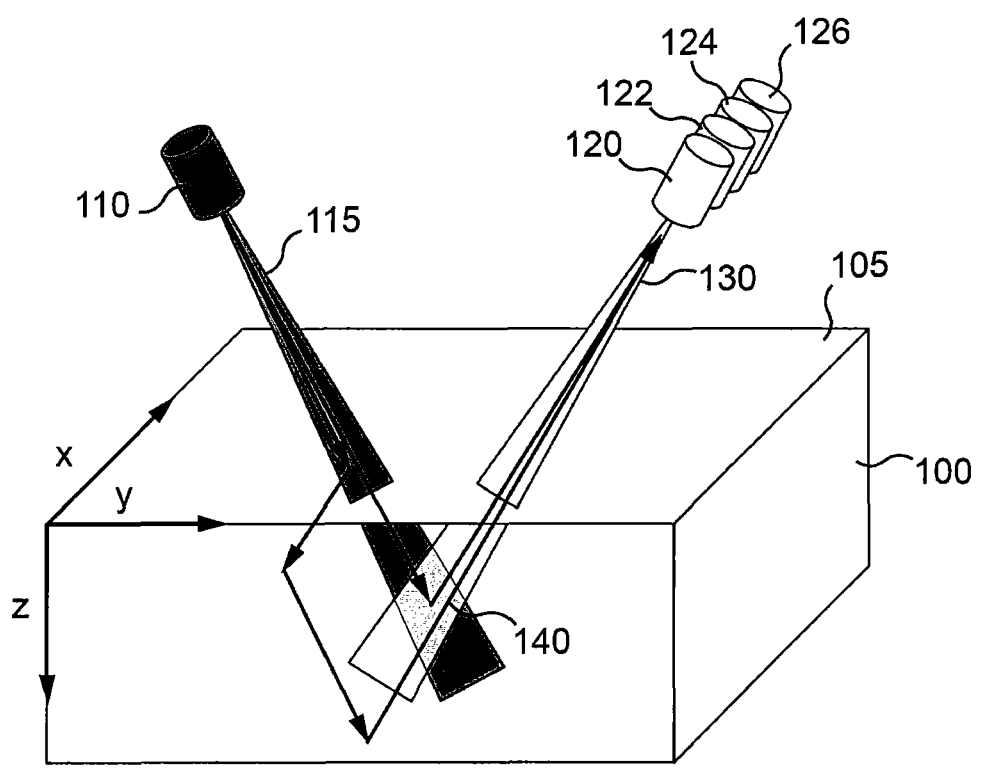
FIG. 1 represents an arrangement implemented in the framework of the invention.
Figure 2:
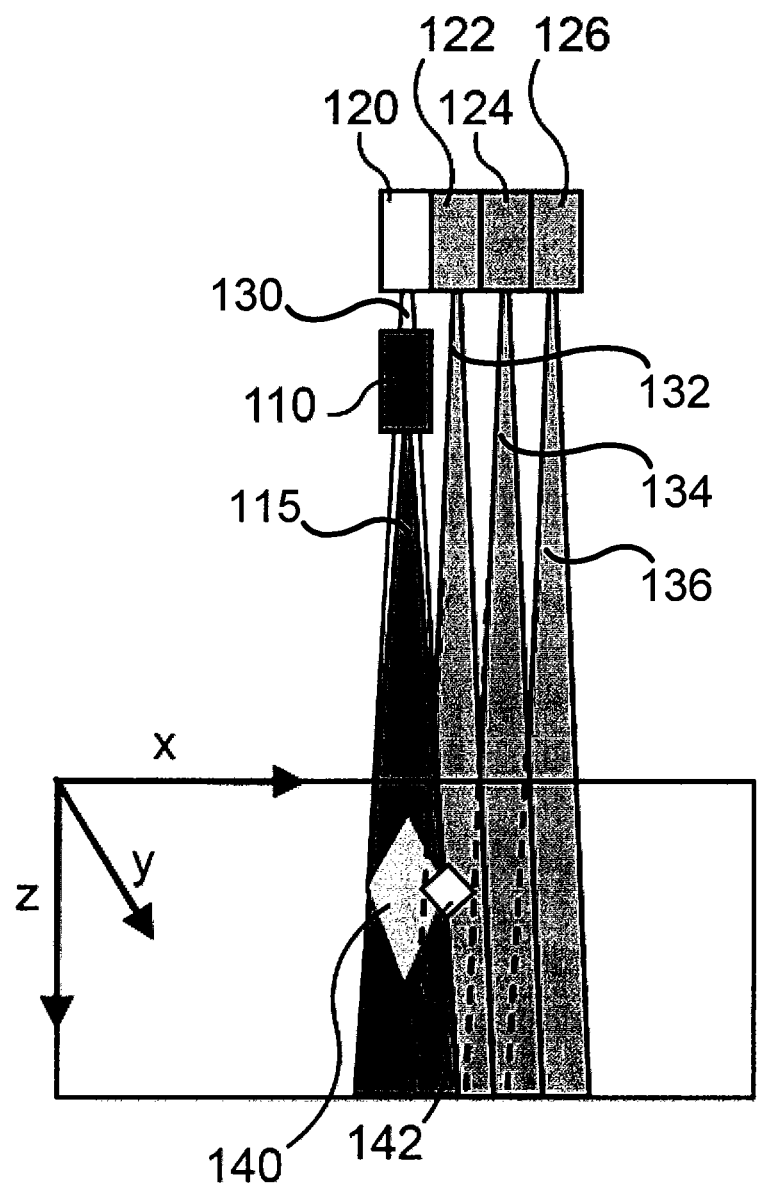
FIG. 2 illustrates the same arrangement seen from a different angle.

FIGS. 1 and 2 illustrate an arrangement for implementing the invention. A parallelepiped volume of material 100 to be analyzed is shown. This material volume 100 has a flat surface 105 defined by axes x an y perpendicular to each other, and depth axis z perpendicular to surface 105.

A source of X rays 110 is directed towards surface 105, and generates an X ray beam 115, called irradiation beam. Source 110 is collimated, and beam 115 has therefore a limited solid opening angle. The irradiation beam 115 has here a central axis arranged in a plane perpendicular to the surface 105, and is inclined in this plane relative to surface 105. Because of the collimation of the source, the irradiation beam is spatially delimited around a central axis, called irradiation beam axis. This irradiation beam, which can also be called irradiation field, can be conical (called irradiation cone), pyramidal, or can have other shapes, according to the geometry of the collimator.

Four radiation detectors, called first, second, third and fourth detector, and respectively designated by the references 120, 122, 124 and 126 are placed opposite surface 105. All four are arranged for measuring a retro-diffuse radiation through the material volume 100. All four are collimated. A field of observation corresponds with each detector, the field of observation corresponds with the solid angle of observation defined by the collimator. This observation field is spatially delimited around a central axis, called observation field axis. Each central axis defines a given angle relative to surface 105. The observation field, which can also be called detection field, can be conical (called observation cone), pyramidal, or can have other shapes, according to the geometry of the collimator.

In the shown implementation mode, each detector has a solid observation angle of surface 105 identical to the solid opening angle of source 110. The observation field of the first detector 120 is referenced 130 and has a central axis which is in the same plane as the central axis of the beam, the irradiation beam 115 emitted by the source. The intersection of the observation field 130 of the first detector 120 and of the irradiation beam 115 of source 110 defines a volume, called inspection volume 140. Indeed, as we will see later, detector 120 performs the inspection of volume 140 of material 100. According to the respective positions and orientations of the source 115 and of the first detector 120, the inspection volume 140 is situated at a certain depth below surface 105 of the analyzed material, called inspection depth.

In the shown implementation mode, all detectors, and the source, are arranged, according to the central axis of their observation field or irradiation beam, at the same distance from the surface of the material.

The observation fields of the second, third and fourth detectors 122, 124 and 126 are referenced 132, 134 and 136 (not shown) and have central axes which are here parallel to the central axis of the observation field of detector 120. These four axes are in addition coplanar in the shown implementation mode. The central axis of observation field 132 meets surface 105 at a distance of 0.5 cm from the point where the observation field axis 130 meets this surface. The central axes of observation fields 134 and 136 act similarly at distances of respectively 1 cm and 1.5 cm. On the other hand, each of the detectors is at the same distance from surface 105, which has as consequence that the intersection surfaces between the observation fields of these detectors and surface 105 are identical in form and dimension.

Observation field 132 has here an intersection volume 142 with beam 115 in the mass of material volume 100. This volume 142 is smaller in volume than previously defined volume 140. On the other hand, observation fields 134 and 136 do not encounter beam 115 in material 100. In this way, the radiation detected by the third and fourth detectors 124 and 126 will not contain primary diffuse radiation. On the other hand, the radiation detected by the first and second detectors 120 and 122 contains a part of primary diffuse radiation, this part is more important for detector 120 than for detector 122.

According to the invention, it is essential that at least one detector has an observation field that intersects the irradiation beam of the source in the analyzed material. The radiation detected by this detector comprises one part of primary diffuse radiation.

It is also advantageous that at least one detector has an observation field that does not intersect the irradiation beam of the source in said material. The radiation detected by this detector does not include primary diffuse radiation, which allows rapid and precise extraction of the primary diffuse radiation spectrum from all of the collected data.

Figure 3:
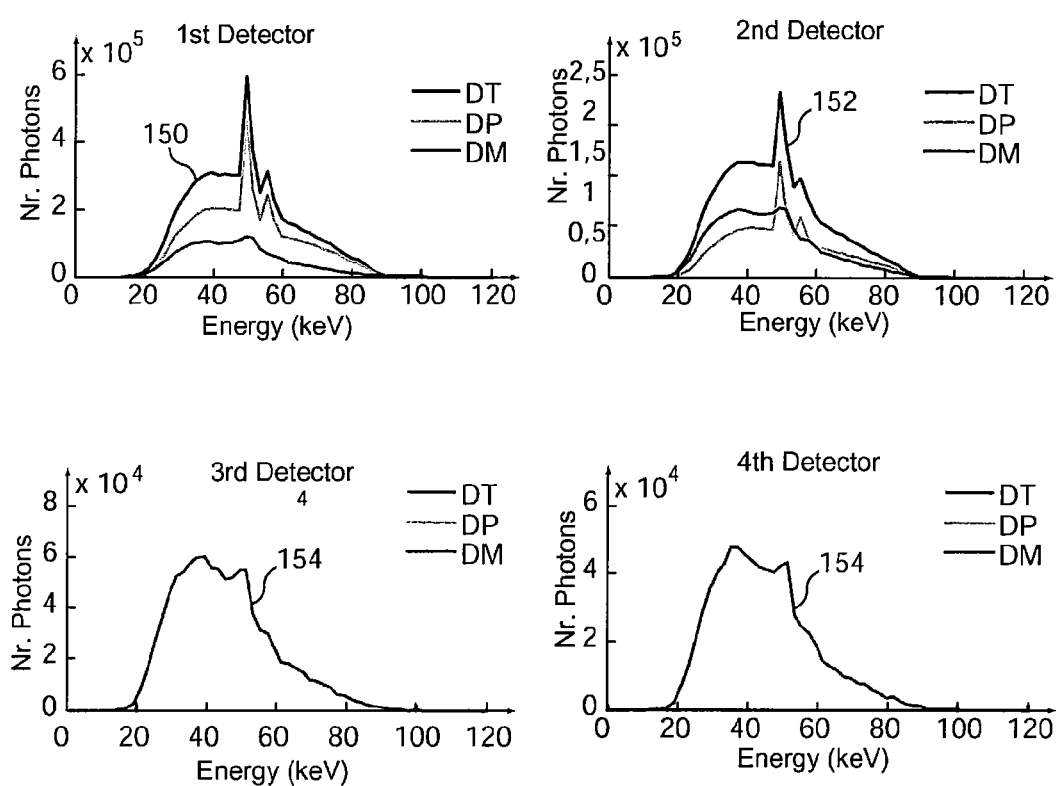
FIG. 3 illustrates the spectra measured by the detectors of the preceding arrangement, and their decomposition between primary diffuse radiation and multiple diffuse radiation.

With reference to FIG. 3, the spectra 150, 152, 154 and 156 measured by the first, second, third and fourth detectors, respectively, of the arrangement of FIGS. 1 and 2, are shown for a sample material. The spectra 150 and 152 comprise a strong component of primary diffuse, visible in particular by the presence of a peak at 50 keV. The two estimated components for each of these two spectra are represented: the primary diffuse component is proportionally more important for spectrum 150 than for spectrum 152. The spectra 154 and 156, of lower overall intensity, have no primary diffuse radiation component.

Figure 4:
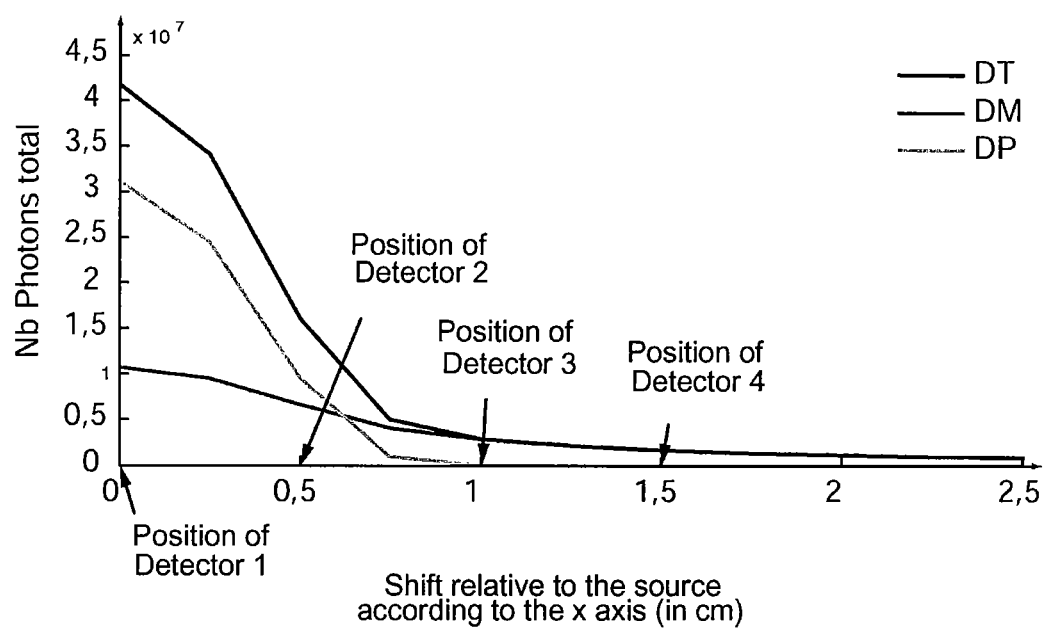
FIG. 4 illustrates the components parts of the primary diffuse radiation and multiple diffuse radiation in the total diffuse radiation spectrum registered by a detector, in function of the position of the detector in the arrangement of FIGS. 1 and 2.

FIG. 4, which is a simulation result, shows in Y-axis the intensity of different diffuse radiation components (primary DP, multiple DM and total DT) present in the signals collected by detectors 120, 122, 124 and 126. The X-axis represents the distance between the intersection point of the central axis of the observation field of the first detector with surface 105 and the intersection points of the central axes of the observation fields of the following detectors with this same surface 105.

Detector 120 collects a total number of photons in the order of $4.2 \times 10^7$, for an acquisition time of 2 minutes, which breaks down in a majority fraction of primary diffuse radiation, close to $3.1 \times 10^7$, and a secondary fraction of multiple diffuse radiation, close to $1.1 \times 10^7$. Detector 122 collects $1.6 \times 10^7$ photons, of which $0.9 \times 10^7$ constitute a signal of primary diffuse radiation, and $0.7 \times 10^7$ a signal of multiple diffuse radiation. Detectors 124 and 126 collect weaker signals, constituted entirely of multiple diffuse radiation.

According to the method, a matrix X is constructed comprising the different spectra measured by the detectors, ordered in rows. Matrix X is written $X=(X_1, X_2, X_3, X_4)^T$, if $X_i$ designates the spectrum obtained by detector i and T the matrix transposition operation. In general manner, if the number of detectors is noted Nd, the matrix is written $X=(X_1 \ldots, X_{Nd})^T$.

The detectors collect photons in discrete channels, the number of which is noted $N_e$, for "number of energy channels." Matrix X is then written:

$$X = \begin{bmatrix} x_{1,1} & \ldots & x_{1,Ne} \\ \ldots & \ldots & \ldots \\ x_{Nd,1} & & x_{Nd,Ne} \end{bmatrix}.$$

According to this notation, each term $X_{ik}$ of matrix X corresponds with a quantity of photons with energy k measured by detector i.

Matrix X is decomposed in two non-negative matrices A and S called weights matrix and spectra matrix, of which the initialization will be described later. The decomposition has the objective of defining two non-negative matrices A and S, so that $X=A \cdot S$. By non-negative matrix (or positive matrix) is understood a matrix of which all terms are positive or zero.

Weights matrix A is, in our example, a matrix with two columns and four rows, the terms of which represent respectively weights of the primary diffuse radiation spectrum and weights of the multiple diffuse radiation spectrum on the four detectors.

In general, weights matrix A has a number of rows equal to the number of detectors, in other words $N_d$. The number of columns of matrix A corresponds to the number of diffuse spectra that we wish to extract, in this case two: a primary diffuse spectrum and a multiple diffuse spectrum. Each element of matrix A is an estimated weight of one of the diffuse radiation components in the signal measured by one of the detectors. Each term $a_{ij}$ of matrix A is the proportion of the diffuse spectrum j (primary diffuse spectrum or multiple diffuse spectrum) measured by detector i.

Spectra matrix S is a matrix with two rows, each representing an estimated spectrum, either of primary diffuse radiation, or multiple diffuse radiation. Matrix S has a number of columns equal to the number of energy channels, or Ne, each spectrum is discrete in the $N_e$ channels. Each term $s_{jk}$ of matrix S is therefore a quantity of photons of spectrum j with energy comprised in the energy range $E_k$ corresponding to channel k.

As previously indicated, matrices A and S are defined so that X≈A·S. The problem comes down to determining the matrices A and S so that a distance between X and the product AS is minimum, with A and S comprising only positive or zero terms. The distance can be expressed by the function ‖X−AS‖², representing an Euclidian distance.

To minimize this function, several methods can be envisaged like for instance a classic gradient descent, under the constraint that A and S are positive (or non-negative). To ensure a good compromise between the rapidity of convergence and ease of implementation, Lee and Seung have proposed multiplicative updating laws, as described in the publication Lee, D. & Seung, H. S., 2001. Algorithms for Nonnegative Matrix Factorization. *Adv. Neural Info. Proc. Syst.*, (13), 556-562.

These updating laws, applied according to an iterative process, are the following $a_{i,j}$ is replaced, with each iteration, by $$a_{i,j} \frac{(XS^T)_{i,j}}{(ASS^T)_{i,j}},$$

then $s_{j,k}$ is replaced, with each iteration, by $$s_{j,k} \frac{(A^T X)_{j,k}}{(A^T AS)_{j,k}},$$

where for a given matrix, the indices i and j refer to an element of the matrix in row i and column j and where T is the symbol of the transposition.

These updating laws ensure that the previously defined function decreases with progressing iterations and converges to a local minimum.

The number of iterations can be fixed arbitrarily, or determined according to a convergence criterion. A convergence criterion can be a threshold E, and the iterative process is stopped when ‖X−AS‖²≤ϵ.

Prior to decomposing matrix X, the weights matrix A and the spectra matrix S used during the first iteration, must be initialized. Of course, this initialization must comply with the constraints of positivity.

These matrices can be initialized arbitrarily, but the inventors have demonstrated that it is preferable that the matrices A and S are initialized as described below.

Figure 5:
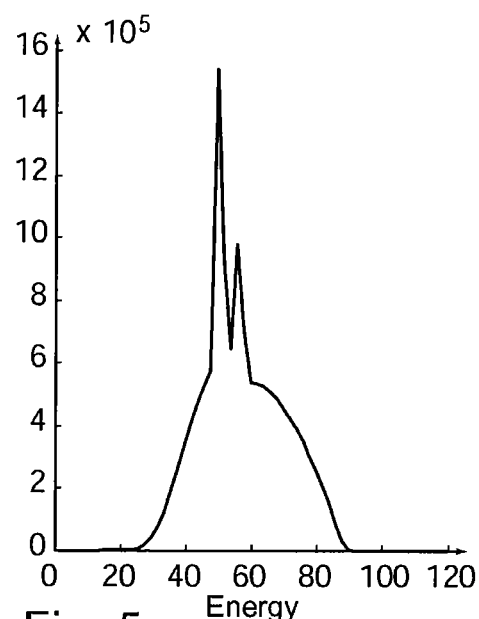
FIG. 5 illustrates a primary diffuse radiation spectrum used for initializing the data used during the method according to the invention.
Figure 6:
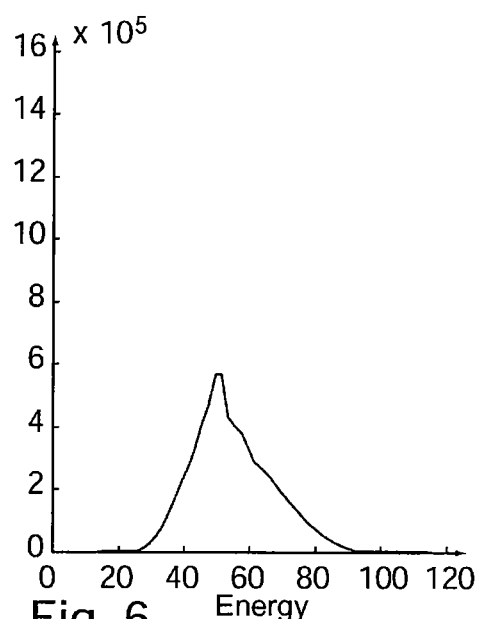
FIG. 6 illustrates a multiple diffuse radiation spectrum used for initializing the data used during the method according to the invention.

By preference, matrix S is initialized with simulated primary and multiple diffuse radiation spectra for a given material. One example is shown in FIG. 5, for the primary diffuse radiation spectrum, which is used for the first line of matrix S. The used material is aluminum. FIG. 6 shows the multiple diffuse radiation spectrum of aluminum, used for initializing the second line of matrix S. This simulated spectrum offers an appearance, or general form, constituting a realistic estimate of the intensity distribution over the different energy channels of the corresponding spectrum of matrix S. To be noted, that the simulation of the exact intensity of the spectrum channels is not a critical parameter in this stage, it is more important to dispose of realistic relative values.

The weights matrix A is initialized taking into account first of all the fact that certain detectors (here third and fourth detectors 124 and 126) cannot receive photons that have experienced only one change in trajectory in the material, because their observation field and irradiation beam have no intersection. In this way, the weight of the primary diffuse radiation spectrum is zero in the spectra measured by these detectors.

Then, for the detectors that are positioned so that they can observe a portion of the primary diffuse radiation spectrum, in other words the detectors that have an observation field intersecting the irradiation beam in the mass of the material, the relationship between the intensity of the multiple diffuse radiation spectrum and the primary diffuse radiation spectrum is determined based on predetermined data stored in a data base, including simulations performed for different materials, and various inspection depths.

Simulations of particle transport based on Monte-Carlo (Géant, MCNP) type protocol or another protocol, in particular the software protocol SindBad used in the presented implementation mode, provide insight in the relationship between the quantity of photons resulting from the primary diffusion and the quantity of photons resulting from the multiple diffusion.

In the presented implementation mode, five materials were used to form a data base. These materials are water ($H_2O$), Plexiglas (registered trademark), Delrin (registered trademark), Kynar (registered trademark) and Teflon (registered trademark). The densities of these materials vary between 1 and 2.2. The data base includes simulations performed for five different depths varying from 1 to 5 cm for each of the materials, with the arrangement described in FIG. 1.

Figure 7:
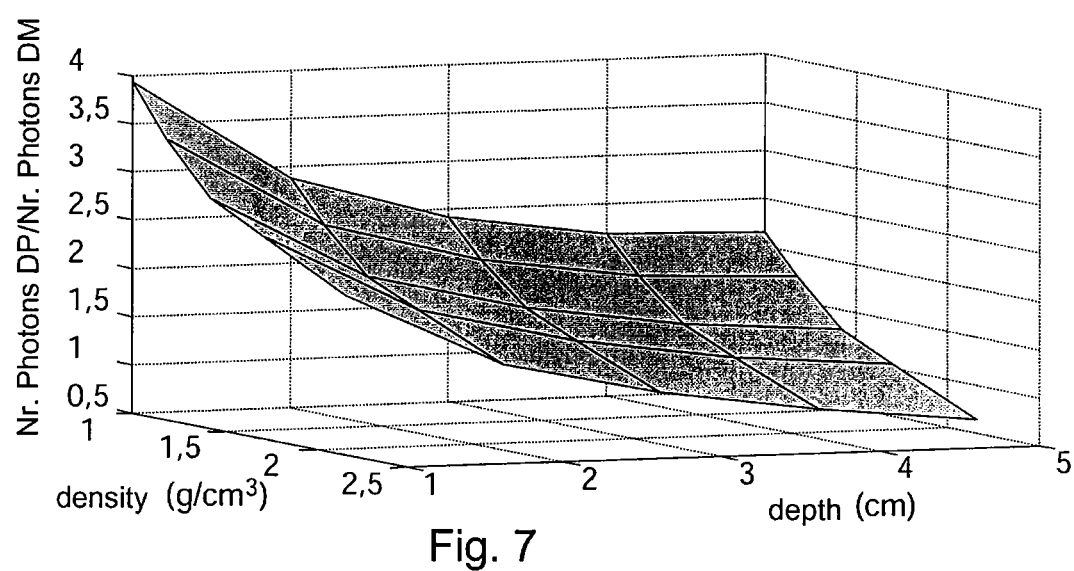
FIG. 7 illustrates the variation of the ratio between the quantity of photons of the primary diffuse radiation and the quantity of photons of the multiple diffuse radiation, in function of the density of the material and the inspection depth, for the first detector of the arrangement of FIGS. 1 and 2.

FIG. 7 shows the tablecloth obtained for the first detector of FIG. 1 representing on the horizontal axis the material density, on the second horizontal axis the inspection depth, and on the vertical axis the ratio between the photons resulting from the primary diffusion and the photons resulting from the multiple diffusion. To be noted, that a maximum is obtained for low densities and minimum depth. For a density equal to 1 and a depth of 1 cm the ratio approaches 4. Inversely, for a depth of 5 cm and a density of 2.5 the ratio is only 0.5.

Figure 8:
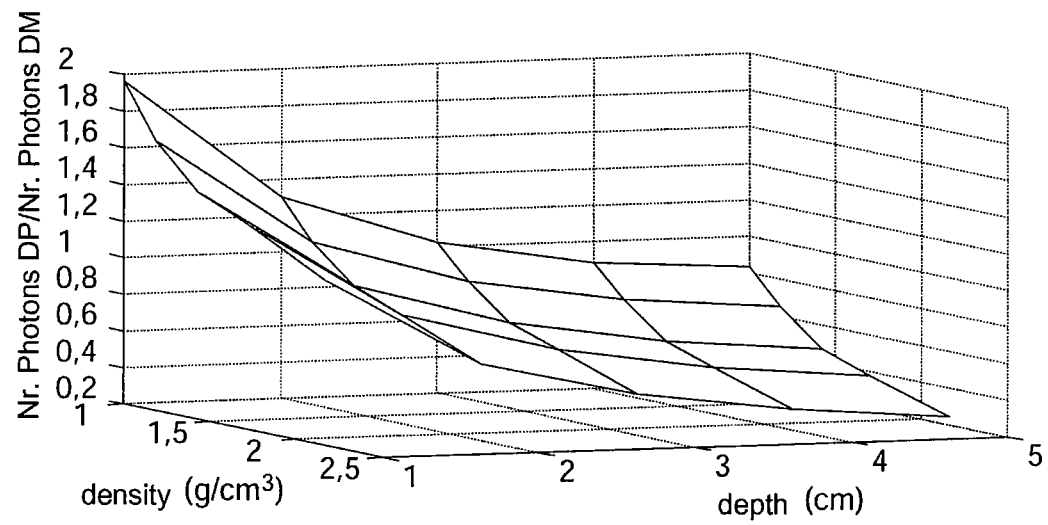
FIG. 8 illustrates the same variation of the ratio between the quantity of photons of the primary diffuse radiation and the quantity of photons of the multiple diffuse radiation, for the second detector of the arrangement of FIGS. 1 and 2.

FIG. 8 shows the tablecloth obtained for a second detector. The horizontal axes represent again density and depth in cm, while the vertical axis represents the ratio of the number of photons resulting from the first diffusion relative to the number of photons resulting from the multiple diffusion. Here also, the maximum values of this ratio are obtained for low densities and low depth. The ratio for a density of 1 and a depth of 1 cm approaches the value 2. Inversely, for a depth of 5 cm and density of 2.5 the ratio is no more than 0.3.

Matrix A is initialized by arbitrarily assigning a value 1 to all weights of the multiple diffuse radiation spectrum. The non zero weights of the primary diffuse radiation spectrum are initialized by reading on the tablecloth corresponding to the detector (in FIG. 7 or FIG. 8), the value of the ratio between the quantity of photons resulting from the primary diffusion relative to quantity of photons resulting from the multiple diffusion. The tablecloth can be approximated by a polynomial, for instance a third degree polynomial, in the sense of least squares.

Figure 9:
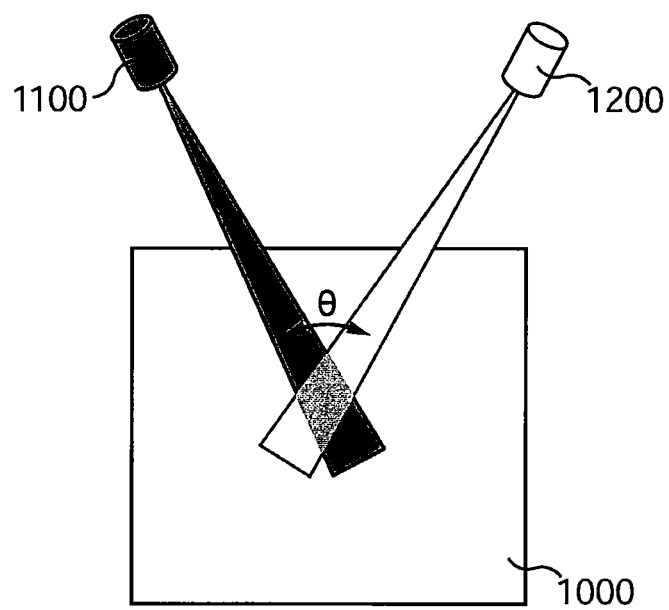
FIG. 9 illustrates an arrangement implementing the invention for analysis of a uniform volume of material.

FIG. 9 shows the experimental device used for studying an homogenous block of Delrin. The Delrin volume is referenced 1000 while the source of X rays is referenced 1100, a detector 1200 is also visible. Three other detectors, oriented parallel to the first detector 1200, are not shown. In this implementation mode the source 1100 is at 23 cm from the material surface, this distance is measured according to the central axis of the X ray beam. The opening angle of the source is 2.4 degrees, the detector 1200 and the three other not shown detectors are cadmium telluride detectors. The four detectors are collimated with an observation angle of 2.4 degrees equal to the angle of the irradiation beam. The angle between the central axis of the irradiation beam and the central axis of the detection field of detector 1200 is 120 degrees. The depth of the inspection volume is 4 cm, volume 1000 is a cube with 8 cm side.

Matrices S and A are initialized with data represented in FIGS. 10 and 11, respectively. Spectrum 2000 is used for initialization of the primary diffuse radiation spectrum and spectrum 2100 is used for initialization of the multiple diffuse radiation spectrum. The weights of the multiple diffuse radiation spectrum in the four detectors are uniformly initialized at 1 as shown by reference 2200 in FIG. 10. The weights of the primary diffuse radiation spectrum are initialized at approximately 1.6; 0.7; 0 and 0 for the first, second, third and fourth detectors, respectively, as indicated by the curve 2300 of FIG. 11.

Figure 12:
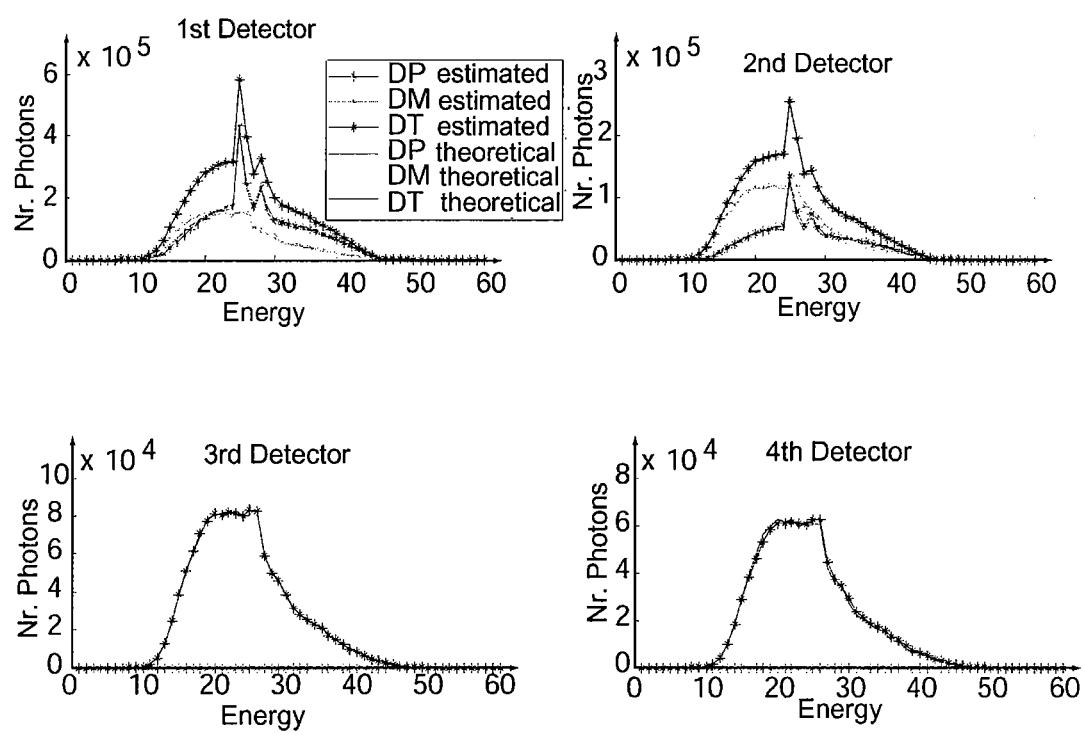
FIG. 12 illustrates the results obtained during the analysis of the material volume of FIG. 9.

FIG. 12 presents the results obtained at the end of 50 iterations for each of the four detectors. In the upper left section of FIG. 12 there is shown the breakdown of the total diffuse radiation spectrum measured by detector 1 (reference 1200, FIG. 9) in its primary diffuse radiation component and its multiple diffuse radiation component. An identical representation is provided in the upper right section of FIG. 12 for the total diffuse radiation spectrum measured by the second detector of the arrangement. To be noted that the primary diffuse radiation component is proportionally weaker in this spectrum than for the spectrum measured by the first detector. The graphs in the lower section of FIG. 12 represent the multiple diffuse radiation spectra measured by the third and fourth detectors, respectively. They are identical, aside from the fact that the intensity of the last spectrum is weaker. All these graphs confront data obtained at the end of the factorization process with theoretical simulation data. It is observed that on all graphs the concordance is excellent.

Figure 13:
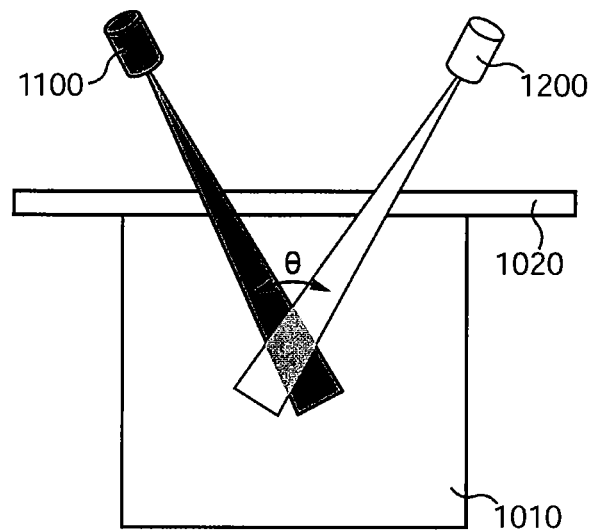
FIG. 13 illustrates an arrangement implementing the invention for analysis of a material volume covered by an external layer of another material.

FIG. 13 shows the arrangement used for a study conducted on a Kynar volume covered by a thin layer of nylon, this layer can represent the exterior surface of bags or suitcases. The Kynar volume is referenced 1110 and the thin layer of nylon is referenced 1020. The solid angles of the irradiation beam and of the detectors as well as the diffusion angle are identical to those shown in the arrangement of FIG. 9. The same applies to the distances between the source and the material. The inspection depth is this time 2 cm, the Kynar volume is a cube with 8 cm side and the nylon layer has a thickness of 4 mm.

Figure 14:
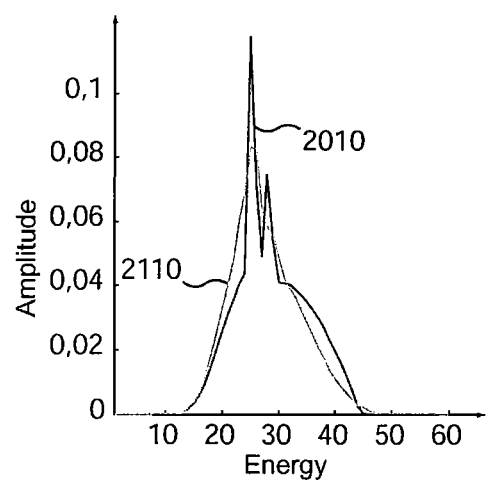
FIG. 14 illustrates the spectra used during the initialization of data for implementing the method according to the invention in the framework of the analysis of the material volume of FIG. 13.
Figure 15:
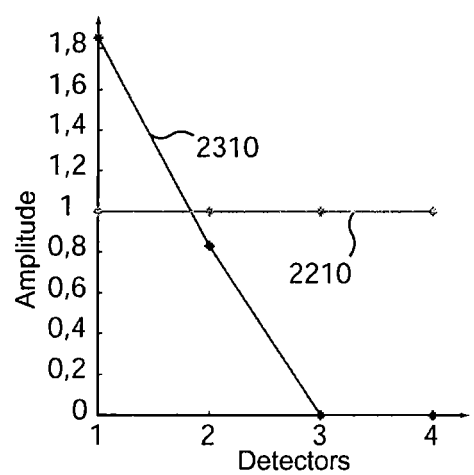
FIG. 15 illustrates data used for implementing the method according to the invention in the framework of the analysis of the material volume of FIG. 13.

Matrix S is initialized with the data shown in FIG. 14 which are composed on the one hand by primary diffuse radiation spectrum 2010 and on the other hand by a multiple diffuse radiation spectrum 2110. Matrix A is initialized with data shown in FIG. 14 where the relative weights of the primary diffuse radiation spectrum of the first and second detectors are selected as 1.85 and 0.8, as shown by reference 2310.

Figure 16:
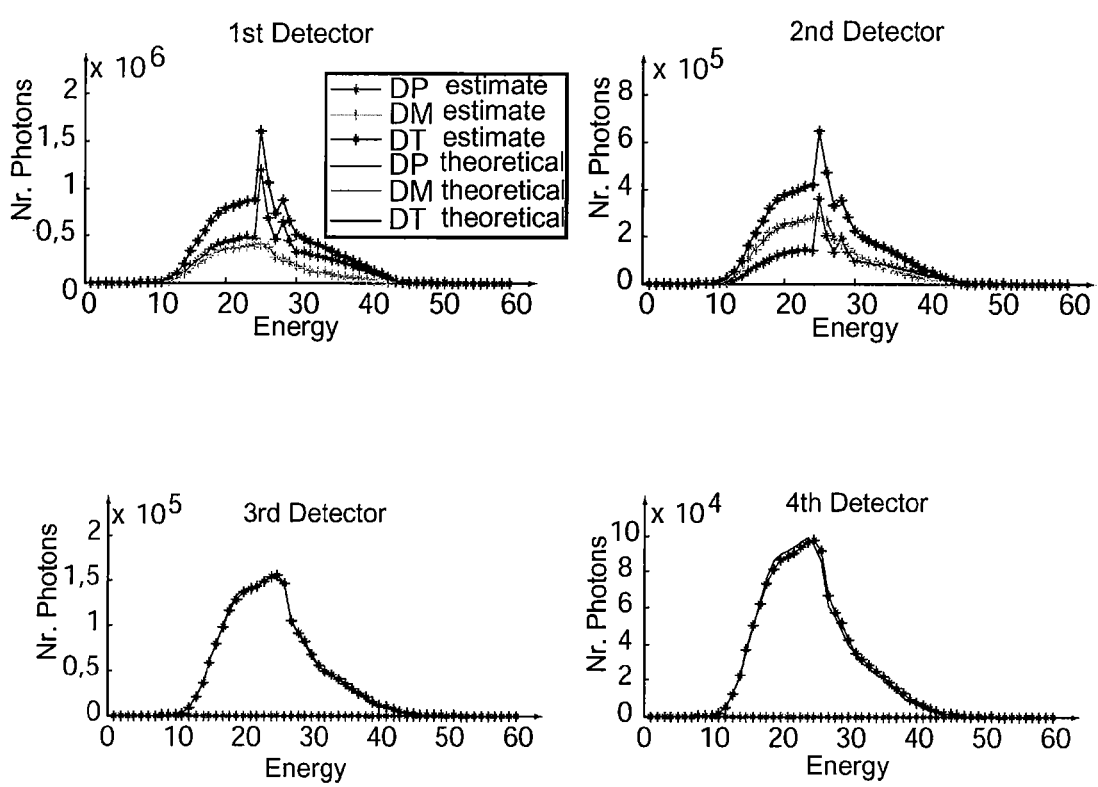
FIG. 16 illustrates the results obtained during the analysis of the material volume of FIG. 13.

FIG. 16 shows the results obtained after convergence of the factorization algorithm, for the four detectors. In the upper left section we observe that for the first detector the primary diffuse radiation component constitutes the majority of the spectrum. While for the spectrum measured by the second detector in the right upper section, the multiple diffuse radiation component is more important. The two figures in the lower section show the spectra measured by the third and fourth detectors, which do not include a primary diffuse component. These two spectra are identical aside from the fact that the intensity of the last spectrum is weaker. The data obtained by the factorization algorithm is confronted with data obtained by simulations based on the theoretical data. It is observed that the data obtained by the method according to the invention and the simulated data are superimposing in excellent manner.

The invention is implemented, in one execution mode, by a software program, for instance stored on readable media by a computer.

Within the scope of variants, instead of using an irradiation beam with the shape of a cone or another volume, a flat irradiation beam can be used. The number of detectors can vary, with observation field axes which are not necessarily coplanar. They can also be disposed for measuring forward diffuse radiation instead of retro-diffuse radiation. In general, the invention is not limited to the described implementation modes and extends to variants within the reach of a person skilled in the art.

The invention claimed is:

1. A method for processing diffuse radiation spectra through a material in order to obtain a primary diffuse radiation spectrum through the material, in which the material is exposed to an incident irradiation beam emitted by a radiation source and at least one diffuse radiation spectrum through the material is measured, the method comprising:
    measuring the primary diffuse radiation spectrum through the material by means of a main detector, arranged so that an observation field of the main detector intersects the incident irradiation beam inside the material;
    measuring at least one secondary spectrum of diffuse radiation through the material by means of at least one secondary detector;
    constructing a measurements matrix (X) starting from a previously measured spectra; and
    decomposing the measurements matrix in two non-negative matrices, including a weights matrix (A) and a spectra matrix (S), wherein the spectra matrix comprises an estimated multiple diffuse radiation spectrum and an estimated primary diffuse radiation spectrum.

2. The method according to claim 1, wherein that at least one secondary detector is arranged so that an observation field does not intersect the incident irradiation beam inside the material.

3. The method according to claim 1 or claim 2 further comprising initializing the weights matrix (A) by extrapolation of data predetermined for a plurality of reference materials prior to decomposing the measurements matrix (X).

4. The method according to claim 3, wherein the extrapolation of data further comprises using an estimate of a density of the material as an extrapolation variable.

5. The method according to claim 1 further comprising initializing the spectra matrix (S) with primary and multiple diffuse radiation spectra simulated for a reference material exposed to the irradiation beam prior to decomposing the measurements matrix (X).

6. The method according to claim 1 comprising an iterative process that further comprises decomposition in non-negative matrices.

7. The method according to the claim 6, wherein the iterative process is continued until a convergence criterion is satisfied related to a proximity between the measurements matrix (X) and a product of non-negative matrices (AS).

8. The method according to claim 1, wherein at least two detectors of the main detector and the secondary detectors are collimated and disposed according to a central axis of the observation field, and at an equal distance from a surface of the material.

9. A computer program product comprising a sequence of instructions stored on a non-transitory computer-readable medium and configured to be executed by a microprocessor for implementing the method according to claim 1.

10. A device for processing diffuse radiation spectra in order to obtain a primary diffuse radiation spectrum through a material, the device comprising:
- a source of radiation suitable for emitting an irradiation beam incident towards the material;
- at least one detector suitable for measuring a diffuse radiation spectrum through the material;
- a first main detector suitable for measuring a primary spectrum of diffuse radiation through the material, and arranged so that an observation field intersects the irradiation beam inside material;
- at least one secondary detector suitable for measuring a secondary spectrum of diffuse radiation through the material;
- a microprocessor for building a measurements matrix (X) starting from measured spectra; and
- software executed by the microprocessor for decomposing the measurements matrix into two non-negative matrices, including a weights matrix (A) and a spectra matrix (S), the spectra matrix comprising an estimated multiple diffuse radiation spectrum and an estimated primary diffuse radiation spectrum.

11. The device according to claim 10, wherein at least one of the secondary detectors is arranged so that an observation field of the detector does not intersect the irradiation beam inside the material.

12. The device according to claim 10, wherein at least two detectors of the main detector and the secondary detectors are collimated with an identical solid observation angle.

13. The device according to claim 10, wherein at least one detector of the main detector or the secondary detectors is collimated and the incident radiation source is collimated, such that the solid angles of the irradiation beam and of an observation field of the at least one detector are identical.

14. The device according to claim 10, wherein the source of irradiation comprises an X ray or gamma ray source.

15. The device according to claim 10, wherein the main detector and the secondary detectors are arranged to measure retro-diffuse radiation.

\* \* \* \* \*